(12) United States Patent
Zeng et al.

(10) Patent No.: US 6,761,838 B2
(45) Date of Patent: *Jul. 13, 2004

(54) CYCLIC AUTOTHERMAL HYDROCARBON REFORMING PROCESS

(75) Inventors: Yongxian Zeng, North Plainfield, NJ (US); Satish S. Tamhankar, Scotch Plains, NJ (US); Narayanan Ramprasad, Hillsborough, NJ (US); Ravi Jain, Bridgewater, NJ (US); Donald L. MacLean, Clinton, NJ (US)

(73) Assignee: The BOC Group, Inc., Murray Hill, NJ (US)

( * ) Notice: Subject to any disclaimer, the term of this patent is extended or adjusted under 35 U.S.C. 154(b) by 346 days.

This patent is subject to a terminal disclaimer.

(21) Appl. No.: 09/909,622

(22) Filed: Jul. 20, 2001

(65) Prior Publication Data

US 2002/0010220 A1 Jan. 24, 2002

Related U.S. Application Data

(63) Continuation-in-part of application No. 09/175,175, filed on Oct. 20, 1998, now Pat. No. 6,379,586.

(51) Int. Cl.[7] .......................... C07C 1/02; C01B 31/18; C01B 3/02
(52) U.S. Cl. .................. 252/373; 423/418.2; 423/648.1
(58) Field of Search .................. 252/373; 423/418.2, 423/648.1

(56) References Cited

U.S. PATENT DOCUMENTS

| | | | |
|---|---|---|---|
| 5,112,590 A | 5/1992 | Krishnamurthy et al. | |
| 5,149,516 A | 9/1992 | Han et al. | |
| 5,538,706 A | 7/1996 | Kapoor et al. | |
| 5,571,492 A | 11/1996 | Yao et al. | |
| 5,714,091 A | 2/1998 | Mazanec et al. | |
| 5,755,840 A | 5/1998 | Beer | |
| 6,379,586 B1 * | 4/2002 | Zeng et al. | 252/373 |

FOREIGN PATENT DOCUMENTS

| | | |
|---|---|---|
| EP | 0 913 184 A1 | 5/1999 |
| JP | 5-4044 | 1/1993 |

OTHER PUBLICATIONS

Patent Abstracts of Japan, vol. 017, No. 266 (C–1062), May 25, 1993 & JP 05 005044 A (Toyoda Gosei Co Ltd.), Jan. 14, 1993 *abstract*.

Editors P.J. Gellings & H.J.M. Bouwmeester, The CRC Handbook Of Solid State Electrochemistry, CRC Press, 1997, Ch. 6, pp. 195–219.

Yue–Sheng Lin, Weijian Wang, and Jonghee Han, "Oxygen Permeation through Thin Mixed–Conducting Solid Oxide Membranes," AiChE Journal, May 1994, vol. 40, No. 5, pp. 786–798.

* cited by examiner

Primary Examiner—Stanley S. Silverman
Assistant Examiner—Jonas N. Strickland
(74) Attorney, Agent, or Firm—Philip H. Von Neida

(57) ABSTRACT

Partial oxidation of hydrocarbons to produce hydrogen and carbon monoxide is carried out by a cyclical process, which includes (a) contacting an oxygen ion conducting ceramic with air at a pressure between about 1 and 50 bara in a reactor, wherein oxygen from the air reacts with the ceramic, thereby producing an oxygen-enriched ceramic, and (b) contacting the hot, oxygen-enriched ceramic with hydrocarbon gas and optionally steam in the reactor. During the partial oxidation reaction phase of the process, the oxygen-enriched ceramic reacts with the hydrocarbon, thereby producing the desired gas products and regenerating the oxygen ion conducting ceramic for the next cycle of the process.

25 Claims, 1 Drawing Sheet

CYCLIC AUTOTHERMAL HYDROCARBON REFORMING PROCESS

RELATED APPLICATION

This application is a continuation-in-part of U.S. patent application Ser. No. 09/175,175 now U.S. Pat. No. 6,379,586 filed on Oct. 20, 1998.

BACKGROUND OF THE INVENTION

1. Field of the Invention

This invention relates to the partial oxidation and/or reforming of hydrocarbons, and more particularly to the production of hydrogen and carbon monoxide by the partial oxidation of hydrocarbons, steam reforming of hydrocarbons or a combination of the two to achieve an auto-thermal process. Specifically, the invention relates to the use of an oxygen ion conducting ceramic in particulate form in a cyclic process, involving the reaction of oxygen in air feed with the ceramic in one step and the reaction of hydrocarbon feed, with or without steam, with the above oxygen-enriched ceramic in another step, to produce hydrogen and carbon monoxide products.

2. Description of Art

Synthesis gas and its components, hydrogen and carbon monoxide, are conventionally produced by the steam methane reforming (SMR) or by the high temperature partial oxidation of hydrocarbons with controlled amounts of air or oxygen. In the SMR process, a large amount of heat must be supplied into the reactor for sustaining the highly endothermic SMR reaction. Therefore, expensive shell-and-tube type reactors must be used to facilitate the heat exchange. The overall production rate of the SMR process is often limited by the heat transfer rate from the shell side to the tube side where the reaction is taking place. In the partial oxidation process, the overall reaction is exothermic, therefore it does not require an external heat supply. However, it does require the use of an oxidant, such as air or oxygen. Although air is less expensive and more convenient to use in partial oxidation reactions, it is less attractive than oxygen because the large quantities of nitrogen that are produced when air is used as the oxidant must be subsequently separated from the product gas prior to its use. The cost of gas separation and purification equipment required to purify the product gas adds considerably to the cost of synthesis gas production using air.

U.S. Pat. No. 5,149,516 to Han et al., discloses a process for the partial oxidation of methane over a perovskite catalyst to produce carbon monoxide and hydrogen. The process involves contacting a source of methane and a source of oxygen together with a perovskite catalyst. The perovskite acts as a catalyst in the reaction of methane and oxygen in a continuous process, i.e. the perovskite does not participate in the reaction, but promotes the reaction rate. In this process, if air is used as the oxygen source, the products (hydrogen and carbon monoxide) will be contaminated with a large amount of nitrogen.

Although oxygen is more desirable than air as an oxidant for partial oxidation reactions, its use involves certain disadvantages. The oxygen must be imported into the system, or it must be generated on site, for example, by means of a cryogenic air separation plant or other means, such as a membrane or a Pressure Swing Adsorption (PSA) system. In either alternative, using oxygen as the oxidant likewise adds considerably to the cost of the process.

More economical methods of on site production of oxygen for applications such as hydrocarbon partial oxidation reactions are continuously sought. U.S. Pat. No. 5,755,840 to Beer discloses a process for providing oxygen to a feed gas, wherein the oxygen is first absorbed from an oxygen-containing gas (e.g., air) by passing the air over an oxygen-sorbent material (e.g., a solid-state lithium cyanocobaltate) until the sorbent material is substantially saturated after which the feed gas (e.g. natural gas) is passed in contact with the sorbent material to desorb the oxygen into the feed gas. This process produces a gaseous mixture of oxygen and natural gas, which will require additional equipment and means to make hydrogen and carbon monoxide products, such as reactors, catalyst and means for heating up the mixture. The sorbent material, such as lithium cyanocobaltate can only adsorb oxygen on its surface at temperatures lower than 100° C.; the lower the temperature, the higher the amount adsorbed.

U.S. Pat. No. 5,714,091 discloses an oxygen-based hydrocarbon partial oxidation process in which the oxygen is produced on site by subjecting air to membrane separation using a membrane constructed of oxygen ion conducting ceramic material. Oxygen, which is permeable to the membrane, passes through the membrane and is made to react with hydrocarbons on the downstream side of the membrane unit. The disadvantages of this method of oxygen production are the high cost of fabrication of the membrane and the difficulty of producing membrane structures that are leak-proof.

The present invention provides a system and process for the partial oxidation of hydrocarbons, steam reforming of hydrocarbons, or a combination of the two to achieve an auto-thermal process in which oxygen is supplied into the reaction from an oxygen-containing gas using a relatively inexpensive particulate oxygen ion conducting ceramic and a simple reactor design. The inventive process is cyclic, wherein oxygen containing gas and hydrocarbon are fed into the reactor in separate steps. In one step, the oxygen ion conducting ceramic selectively reacts with molecular oxygen at high temperatures by dissociating gas phase oxygen molecules into oxygen ions at its surface and then incorporating these ions into its lattice structure by means of ion conduction through the oxygen vacancies in its lattice structure. This results in the formation of an oxygen-enriched ceramic. In another step, the oxygen-enriched ceramic reacts with hydrocarbon feed to form a product containing hydrogen and carbon monoxide. The process of this invention has several advantages, namely: (1) the separation of oxygen from oxygen-containing gas is conducted in the same vessel as that used for the partial oxidation of hydrocarbons; (2) there is no oxygen in the gas phase during the partial oxidation of hydrocarbons, providing a much safer operating environment; and (3) oxygen ion conducting ceramic in a particulate form is easier to fabricate and costs much less than one in a membrane form. In addition, the process has the advantage that the heat produced during the step in which oxygen reacts with the oxygen ion conducting ceramic can be used to increase the overall efficiency of the process by maintaining the ceramic at the desired temperature without an external heat source and it can also be used to preheat incoming feed streams, by way of heat exchange means.

SUMMARY OF THE INVENTION

According to a broad embodiment, the invention includes a process for producing hydrogen and carbon monoxide by the partial oxidation of at least one hydrocarbon comprising the steps of:

(a) contacting an oxygen ion conducting ceramic in particulate form in a reactor with an oxygen-containing gas at a temperature in the range between about 300 and 1400° C. and at a pressure in the range between about 1 and 50 bara, wherein oxygen from the oxygen-containing gas is reacted with the ceramic, thereby producing an oxygen-enriched ceramic; and (b) contacting the oxygen-enriched ceramic in the reactor with a hydrocarbon at a temperature in the range between about 300 and 1400° C., thereby producing a product gas through the reaction between the oxygen-enriched ceramic and the hydrocarbon;

wherein step (b) is conducted at a pressure of between about 1 and 50 bara.

Another embodiment of the present invention includes a process for the continuous production of hydrogen and carbon monoxide by the partial oxidation of at least one hydrocarbon, using two reactors, comprising the steps of:

(a) in a first reactor, contacting a first oxygen ion conducting ceramic with an oxygen-containing gas at a temperature in the range between about 300 and 1400° C. and at a pressure in the range between about 1 and 50 bara, wherein oxygen from the oxygen-containing gas reacts with the first ceramic, thereby producing a first oxygen-enriched ceramic; and contacting the first oxygen-enriched ceramic with the hydrocarbon at a temperature in the range between about 300 and 1400° C., thereby producing a first product gas; and (b) in a second reactor, contacting a second oxygen ion conducting ceramic with an oxygen-containing gas at a temperature in the range between about 300 and 1400° C. and at a pressure in the range between about 1 and 50 bara, wherein oxygen from the oxygen-containing gas reacts with the second ceramic, thereby producing a second oxygen-enriched ceramic; and contacting the second oxygen-enriched ceramic with the hydrocarbon at a temperature in the range between about 300 and 1400° C., thereby producing a second product gas.

The continuous production process may be operated wherein the first reactor is 180° out of phase with the second reactor, whereby either:

(a) the first product gas is being formed in and removed from the first reactor while the oxygen from oxygen-containing gas is reacting with the second ceramic in the second reactor; or (b) oxygen from oxygen-containing gas is reacting with the first ceramic in the first reactor while the second product gas is being formed in and removed from the second reactor.

Continuous production can be achieved by using two or more reactors operated in parallel. The number of reactors is a matter of selection; the number of reactors and the operating sequence can be selected to optimize the continuous production of hydrogen and carbon monoxide. With multiple reactors the operating sequence will need to be modified to achieve the desired productivity and to maintain all the reactors in thermal balance. This is accomplished by generally known methods used in practice.

In another embodiment, the present invention includes a system for the continuous production of a product gas from the partial oxidation of at least one hydrocarbon, the system comprising:

(a) a first reactor comprising a first oxygen ion conducting ceramic;

(b) means for contacting the first oxygen ion conducting ceramic with an oxygen-containing gas at a temperature in the range between about 300 and 1400° C. and at a pressure in the range between about 1 and 50 bara, wherein oxygen from the oxygen-containing gas reacts with the first ceramic, thereby producing a first oxygen-enriched ceramic;

(c) means for contacting the first oxygen-enriched ceramic with the hydrocarbon at a temperature in the range between about 300 and 1400° C., thereby producing a first product gas;

(d) a second reactor comprising a second oxygen ion conducting ceramic;

(e) means for contacting the second oxygen ion conducting ceramic with an oxygen-containing gas at a temperature in the range between about 300 and 1400° C. and at a pressure in the range between about 1 and 50 bara, wherein oxygen from the oxygen-containing gas reacts with the second ceramic, thereby producing a second oxygen-enriched ceramic; and (f) means for contacting the second oxygen-enriched ceramic with the hydrocarbon at a temperature in the range between about 300 and 1400° C., thereby producing a second product gas.

The system of the present invention may further comprise a first means for removing the first product gas from the first reactor and a second means for removing the second product gas from the second reactor, wherein the first and second removing means can be either different or the same.

In another preferred embodiment, the system includes at least one means, such as a heat exchanger, for heating the oxygen-containing gas, the hydrocarbon gas, and combinations thereof.

The process of the present invention can be used to produce product gases other than synthesis gas by disposing or mixing a catalyst with the oxygen ion conducting ceramic.

In one embodiment of the present invention there is included a process for the production of cyclic anhydrides via partial oxidation of at least one hydrocarbon comprising the steps of:

(a) contacting an oxygen ion conducting ceramic having an anhydride-forming catalyst disposed thereon with an oxygen-containing gas at a temperature in the range between about 250 and 650° C. and at a pressure in the range between about 1 and 50 bara, wherein oxygen from the oxygen-containing gas reacts with the ceramic, thereby producing an oxygen-enriched ceramic; and (b) contacting the oxygen-enriched ceramic with hydrocarbon at a temperature in the range between about 250 and 650° C., thereby producing cyclic anhydrides.

In a preferred embodiment of the process to produce cyclic anhydrides, the anhydride-forming catalyst is a vanadium-based catalyst.

In another embodiment of the present invention, there is included a process for the production of alkylene oxides via partial oxidation of at least one hydrocarbon comprising the steps of:

(a) contacting an oxygen ion conducting ceramic having an alkylene-forming catalyst disposed thereon with an oxygen-containing gas at a temperature in the range between about 250 and 650° C. and at a pressure in the range between about 1 and 50 bara, wherein oxygen from the oxygen-containing gas reacts with the oxygen ion conducting ceramic, thereby producing an oxygen-enriched ceramic; and (b) contacting the oxygen-enriched ceramic with hydrocarbon at a temperature in the range between about 250 and 650° C., thereby producing alkylene oxides.

In a preferred embodiment of the process to produce alkylene oxides, the alkylene-forming catalyst is a silver oxide catalyst.

In another embodiment of the present invention, there is included a process for the production of chlorinated hydrocarbons via partial oxidation of at least one hydrocarbon comprising the steps of:

(a) contacting an oxygen ion conducting ceramic having a chlorinated hydrocarbon-forming catalyst disposed thereon with an oxygen-containing gas at a temperature in the range between about 250 and 650° C. and at a pressure in the range between about 1 and 50 bara, wherein oxygen from the oxygen-containing gas reacts with the oxygen ion conducting ceramic, thereby producing an oxygen-enriched ceramic; and (b) contacting the oxygen-enriched ceramic with hydrocarbon at a temperature in the range between about 250 and 650° C., thereby producing chlorinated hydrocarbons.

In a preferred embodiment of the process to produce chlorinated hydrocarbons, the chlorinated hydrocarbon-forming catalyst is a copper chloride catalyst.

In another embodiment of the present invention, there is included a process for the production of aldehydes via partial oxidation of at least one hydrocarbon comprising the steps of:

(a) contacting an oxygen ion conducting ceramic having an aldehyde-forming catalyst disposed thereon with an oxygen-containing gas at a temperature in the range between about 250 and 650° C. and at a pressure in the range between about 1 and 50 bara, wherein oxygen from the oxygen-containing gas reacts with the oxygen ion conducting ceramic, thereby producing an oxygen-enriched ceramic; and (b) contacting the oxygen-enriched ceramic with hydrocarbon at a temperature in the range between about 250 and 650° C., thereby producing aldehydes.

In a preferred embodiment of the process to produce aldehydes, the aldehyde-forming catalyst is a catalyst selected from the group consisting of: copper chloride, palladium chloride, molybdenum, bismuth, iron, and mixtures thereof.

In another embodiment of the present invention, there is included a process for the production of olefinically unsaturated nitriles via partial oxidation of at least one hydrocarbon comprising the steps of:

(a) contacting an oxygen ion conducting ceramic having a nitrile-forming catalyst disposed thereon with an oxygen-containing gas at a temperature in the range between about 250 and 650° C. and at a pressure in the range between about 1 and 50 bara, wherein oxygen from the oxygen-containing gas reacts with the oxygen ion conducting ceramic, thereby producing an oxygen-enriched ceramic; and (b) contacting the oxygen-enriched ceramic with hydrocarbon at a temperature in the range between about 250 and 650° C., thereby producing olefinically unsaturated nitrites.

In a preferred embodiment of the process to produce olefinically unsaturated nitrites, the nitrile-forming catalyst is a catalyst selected from the group consisting of: bismuth-molybdenum oxide catalyst and iron-antimony oxide catalyst.

DETAILED DESCRIPTION OF THE INVENTION

Figure 1:
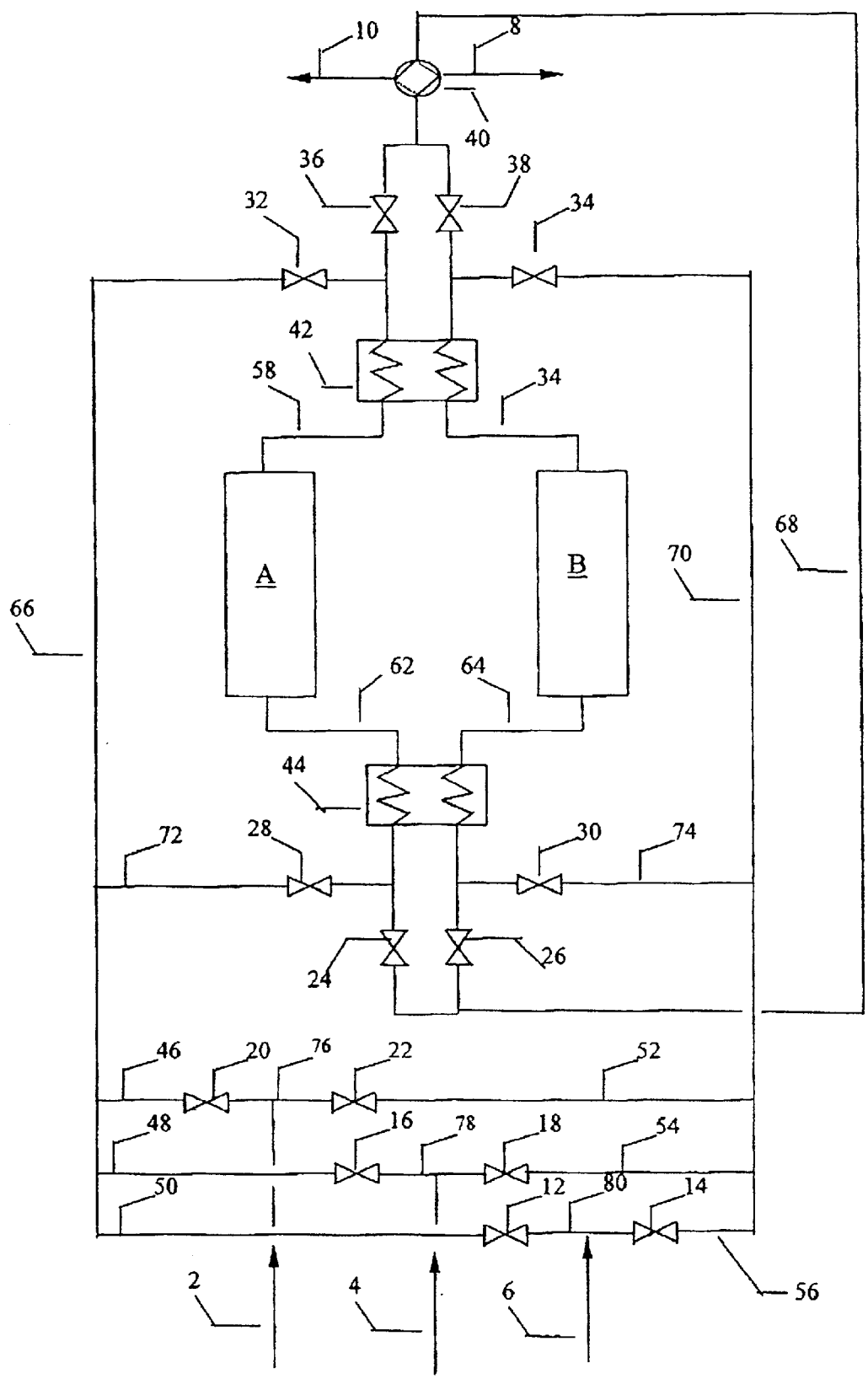
FIG. 1 is a schematic representation of a two-reaction vessel system for the practice of the process of the invention.

The process of the invention is useful for carrying out partial oxidation processes that produce hydrogen and/or carbon monoxide and perhaps other products using air as the oxidant without diluting the products with nitrogen. The process of the invention is particularly useful for economically conducting partial oxidation processes in systems of any desired size. The oxygen-containing gas reacts with an oxygen ion conducting ceramic at high temperatures. The heat produced during the step of oxygen reacting with the oxygen ion conducting ceramic provides a high temperature environment for the partial oxidation process in the subsequent step.

The oxygen from an oxygen-containing gas reacts with the oxygen ion conducting ceramic and produces an oxygen-enriched ceramic by dissociating oxygen molecules into oxygen ions and incorporating these oxygen ions into the lattice structure of the ceramic. By "oxygen-containing gas" it is meant a gas that contains elemental oxygen. The oxygen-containing gas may be, for example, substantially pure oxygen or an oxygen-gas mixture, such as, oxygen-nitrogen mixtures, oxygen-argon mixtures, oxygen-nitrogen-argon mixtures, air, oxygen-carbon dioxide mixtures, oxygen-carbon monoxide mixtures, etc. The preferred oxygen-containing gas is air, because of its low cost and ready availability. The oxygen-containing gas can also be a gas containing molecularly bound oxygen, such as, for example, steam, $CO_2$, $SO_2$, $NO_x$, $SO_x$, and combinations thereof. Preferred among these are steam and $CO_2$. In this case, oxygen is extracted from the molecule, such as from $H_2O$ or $CO_2$, producing $H_2$ or CO in the process as additional useful by-products.

The process of the invention is preferably carried out in a cyclical fashion. It comprises a step of reacting oxygen from oxygen containing gas with oxygen ion conducting ceramic at high temperature to make the oxygen-enriched ceramic and a partial oxidation reaction step of reacting the oxygen-enriched ceramic with hydrocarbon(s) and regenerating the oxygen ion conducting ceramic. The process can be carried out in a system comprising a single reactor unit or a battery of reactor units operated in phase, or batteries of reactor units operated out of phase, whichever is desired. When a system comprising a single unit or a battery of units, all of which are operated in phase, is used, the two steps are necessarily intermittent. When a plurality of units are employed in parallel and operated out of phase, one or more units can be fed oxygen-containing gas while the partial oxidation reaction is being carried out in one or more other units. In preferred embodiments of the invention, the two steps of the cycle are repeatedly carried out in a manner such that production of the desired partial oxidation products is essentially continuous.

The ceramic material used in the process of this invention is an oxygen ion conducting ceramic. By "oxygen ion conducting ceramic" it is meant a ceramic material that exhibits oxygen ion conductivity at high temperature. It also includes oxygen selective mixed conductors, which have both oxygen ion conductivity and electronic conductivity at high temperature. Properties of oxygen ion conducting ceramic conductors are set forth in "The CRC Handbook of Solid State Electrochemistry" edited by P. J. Gellings and H. J. M. Bouwmeester, published in 1997, pp. 195–219, the text of which is incorporated herein by reference.

Preferred oxygen ion conducting ceramics include, for example, materials selected from: (1) perovskite substances having the structural formula $ABO_3$ where A is at least one metal ion capable of occupying the 12-coordinate sites of the perovskite structure and B is at least one metal ion capable of occupying the 6-coordinate sites of the perovskite structure; (2) ceramic materials selected from compounds such as $Bi_2O_3$, $ZrO_2$, $CeO_2$, $ThO_2$, $HfO_2$ and mixtures of these, wherein the ceramic material is doped with CaO, a rare earth metal oxide, such as, for example, $Y_2O_3$, $Nb_2O_3$, $Sm_2O_3$, $Gd_2O_3$ and mixtures thereof; (3) a brownmillerite oxide; and (4) mixtures of any of (1) through (3).

In a preferred embodiment, the oxygen ion conducting ceramic is a ceramic substance having the above-described perovskite structure, where A is at least one metal ion selected from alkali, alkaline earth and rare earth ions, and B is at least one metal atom selected from transition metal ions. More preferably, A is La, Y, Sr, Ca, Ba, Mg or mixtures thereof, B is selected from Co, Mn, Cr, Ni, Fe or mixtures of these.

Typical perovskite ceramics suitable for use in the invention have the general formula: $La_{(1-x)}Sr_xBO_3$, $Y_{(1-x)}Sr_xBO_3$, $Y_{(1-x)}Ca_xBO_3$ and combinations thereof, wherein B is Co, Mn, Cr, Ni or Fe. Specific useful perovskite ceramics are materials having the structural formulas: $La_{0.8}Sr_{0.2}MnO_3$, $La_{0.7}Ca_{0.3}FeO_3$, $Y_{0.9}Sr_{0.1}CrO_3$, $SrCoO_3$, etc. In the last compound, $SrCoO_3$, x has a value of 1.

The major chemical reactions taking place during the invented process can be described as follows, when air is used as the oxygen-containing gas and methane and steam are introduced in the partial oxidation step:

Air step: $P+O_2$ (air)$\rightarrow$P—O+$N_2$ (exothermic);

Partial oxidation step: P—O+$CH_4$$\rightarrow$P+CO+$2H_2$ (exothermic or endothermic, depending on the P—O stoichiometry); and Steam methane reforming reaction occurring in parallel with the partial oxidation reaction: $CH_4+H_2O\rightarrow CO+3H_2$ (endothermic), where P and P—O represent oxygen-depleted and oxygen-enriched perovskite-type oxide, respectively.

In addition, water-gas shift reaction can occur producing more hydrogen as follows:

$$CO+H_2O\rightarrow CO_2+H_2$$

The minimum temperature for the oxygen step at which oxygen reacts with the oxygen ion conducting ceramic is generally at least about 200° C. This step is preferably carried out at temperatures of at least about 300° C., and most preferably carried out at temperatures of at least about 500° C. The upper temperature limit for carrying out this step is below the temperature at which the oxygen ion conducting ceramic begins to melt. Generally, the maximum upper temperature is not in excess of about 1400° C. Preferably, the oxygen step is carried out at temperatures not exceeding about 1200° C., and this step is most preferably carried out at temperatures not in excess of about 1100° C.

Since the oxygen step of the process is highly exothermic, the temperature in the reaction zone tends to rise as this step proceeds. It is often desirable to recover the significant quantity of heat generated during the process. This can be conveniently accomplished by including one or more thermal ballast in the system. The ballast may be, for example, in the form of particulate materials having high heat capacity. The high heat capacity material may be mixed with the oxygen ion conducting ceramic, or it may comprise an independent layer upstream and/or downstream of the layer of the oxygen ion conducting ceramic material. In the latter alternative, it is often desirable to position the layer of high thermal conductivity material on the downstream side of the oxygen ion conducting ceramic with respect to the direction of flow of gas through the reaction vessel during the oxygen step of the process. As such, heat can be captured from the hot gases leaving the reaction zone during the oxygen step. This serves the dual purpose of cooling the effluent stream and storing heat for use in heating hydrocarbon feed being fed into the reaction zone during the following partial oxidation step of the process.

The partial oxidation step of the process is generally carried out at or near the temperature at which the oxygen step is carried out. The overall reaction in the partial oxidation step could be exothermic, endothermic, or thermally neutral.

The particular hydrocarbon or hydrocarbons used as a reactant in the hydrocarbon partial oxidation step of the process of the invention is a matter of choice. When the partial oxidation process is used to simply produce hydrogen and carbon monoxide, the hydrocarbon used as feed may be any aliphatic, cycloaliphatic or aromatic hydrocarbon having 1 to 12 or more carbon atoms, and it may be saturated or ethylenically unsaturated and straight chain or branched chain. Preferred hydrocarbons are the aliphatic hydrocarbons having 1 to 6 carbon atoms, and more preferred hydrocarbon feeds are comprised of one or more hydrocarbons having 1 to 4 carbon atoms. Suitable hydrocarbon feed substances include, for example, methane, methanol, ethane, propane, butane, benzene, xylene, refined petroleum derivatives, such as, naphtha and gasoline, diesel and mixtures thereof. Preferred hydrocarbon feeds include methane, methanol, ethane, ethene, propane, propene, $C_4$ hydrocarbons, and mixtures thereof. Most preferred hydrocarbon feeds for the production of hydrogen and carbon monoxide, by the process of the invention, are methane, natural gas, and mixtures thereof.

If desired, the partial oxidation step of the process can be used to produce partial oxidation products other than carbon monoxide and hydrogen. This can be accomplished by including in the reaction vessel a catalyst, deposited on or mixed with the oxygen ion conducting ceramic, which promotes the desired partial oxidation reaction and by using the appropriate hydrocarbon as the feed stream. Typical of such partial oxidation product manufacturing processes include, for example:

1. The manufacture of cyclic anhydrides by the reaction of aromatic compounds or straight-chained $C_4$ hydrocarbons with oxygen-enriched ceramic in the presence of a vanadium-based catalyst. Examples include the production of maleic anhydride by the reaction of benzene or a saturated or unsaturated $C_4$ hydrocarbon such as butane or butene with oxygen-enriched ceramic and the manufacture of phthalic anhydride by the reaction of p-xylene or naphthalene with oxygen.

2. The manufacture of alkylene oxides by the reaction of lower alkanes or alkenes with oxygen-enriched ceramic in the presence of a silver oxide catalyst supported on silica or alumina or mixed molten nitrate salts. An example is the reaction of propane or propylene with oxygen-enriched ceramic in the presence of molten sodium and potassium nitrates to produce propylene oxide.

3. The manufacture of chlorinated hydrocarbons by the reaction of lower alkanes or alkenes with oxygen-enriched ceramic and hydrogen chloride or chlorine in the presence of a copper chloride catalyst supported on silica or alumina. Examples include the reaction of ethylene or ethane with oxygen-enriched ceramic and hydrogen chloride or chlorine to produce vinyl chloride or ethylene dichloride.

4. The manufacture of aldehydes by the reaction of lower alkanes or alkenes with oxygen-enriched ceramic in the presence of various metal halides or metal oxide catalysts. Examples include the production of acetaldehyde by the reaction of ethylene with oxygen-enriched ceramic in the presence of copper chloride and palladium chloride, and the manufacture of acrolein by the reaction of propane or propylene with oxygen-enriched ceramic over a molybdenum-bismuth-iron catalyst.

5. The manufacture of olefinically unsaturated nitrites by the reaction of lower alkanes or alkenes with oxygen-enriched ceramic and ammonia in the presence of a bismuth molybdenum oxide catalyst or an iron antimony oxide catalyst supported on silica or alumina. Examples of this type of process include the production of acrylonitrile by the reaction of propane or propylene with oxygen-enriched ceramic and ammonia and the production of methacrylonitrile by the reaction of i-butane or i-butylene with oxygen-enriched ceramic and ammonia.

When the partial oxidation process is used to produce compounds other than hydrogen and carbon monoxide, the feed hydrocarbon may be one or more aromatic, aliphatic or cycloaliphatic compounds, and it may be saturated or ethylenically unsaturated and straight chain or branched. Suitable aromatic hydrocarbons include those having up to 12 or more carbon atoms and suitable aliphatic and cycloaliphatic hydrocarbons include those having 2 to 12 or more carbon atoms. Preferred aromatic hydrocarbons are those having 6 to 10 carbon atoms, such as, benzene, xylene and naphthalene, and preferred aliphatic hydrocarbons are the saturated or ethylenically unsaturated straight-chain hydrocarbons having 2 to 6 hydrocarbon atoms, such as, ethane, ethene, propane, propylene, n-butane, i-butane, n-butylene, i-butylene, butadiene, pentane, pentene, hexane and hexene.

It may be desirable to include a purge step after the partial oxidation step of the process but before the oxygen step of the next succeeding cycle to recover or remove any product gas remaining in the reaction chamber after the partial oxidation step. Suitable purge gas should be a gas compatible with the process, such as, for example, carbon dioxide, steam, nitrogen, argon helium, and mixtures thereof.

In a variation of the partial oxidation reaction described above, a moderating agent, such as water, preferably in the form of steam, carbon dioxide or a mixture thereof, can be passed through the reaction zone along with the hydrocarbon. In this variation, steam- or carbon dioxide-reforming of the hydrocarbon occurs in addition to partial oxidation of the hydrocarbon. The steam and/or carbon dioxide reforming reaction can take place even after substantially all of the free lattice oxygen is consumed by the partial oxidation reaction.

The invention can be more easily understood by reference to the appended drawing, considered in conjunction with the following description. Equipment that is not necessary for an understanding of the invention, such as, auxiliary valves, pumps, and storage vessels, has not been included in the illustrated system.

Turning now to FIG. 1, illustrated therein is a two-vessel partial oxidation system, having reaction vessels A and B arranged in parallel. Vessels A and B are packed with a particulate oxygen ion conducting ceramic, for example, a perovskite ceramic material of the type described above. The system is provided with air feed line 2, methane feed line 4 and steam feed line 6, which are connected respectively to manifolds 76, 78 and 80. These manifolds are in fluid communication with heat exchangers 42, 44 through various valves, as described below, such that any of the feed gases can flow through either of the heat exchangers in any desired direction. Heat exchangers 42, 44 are in fluid communication with vessels A and B. Thus, heat exchanger 42 is connected to vessel A through line 58 and to vessel B through line 34. Likewise, heat exchanger 44 is connected to vessel A through line 62 and to vessel B through line 64.

The system is provided with line 8 to carry away the product generated in the reaction step (e.g. synthesis gas in the case of hydrocarbon partial oxidation) and line 10 to carry away the non-absorbed waste gas stream generated in the absorption step (e.g. nitrogen, when air is used as the oxygencontaining gas). Lines 8 and 10 are connected to the system through 4-way selection valve 40 which can be in fluid communication with heat exchanger 42 through valve 36 or valve 38, and with heat exchanger 44 through valve 24 or valve 26.

The system illustrated in the drawing is designed to be operated in semi-continuous or continuous fashion, with vessels A and B being operated 180° out of phase, so that in one vessel oxygen is reacting with an oxygen ion conducting ceramic while the other vessel is in partial oxidation reaction service, and vice versa. The process of the invention, as carried out in the system illustrated in the drawing, will be described as a two-stage process comprising a first stage, in which vessel A is reacting oxygen with an oxygen ion conducting ceramic and vessel B is in partial oxidation reaction mode, and a second stage, in which vessel B is reacting oxygen with an oxygen ion conducting ceramic and vessel A is in partial oxidation mode.

At the beginning of the first stage, valves 20, 32, 24, 18, 30, 38, and optionally 14, are open and all other valves are closed. Air, introduced into the system through line 2 at desired pressure, passes sequentially through valve 20, lines 46 and 66, valve 32, heat exchanger 42 and line 58, and enters vessel A. An air-drying step is not ordinarily necessary or desirable in the process of the invention, since primarily only oxygen will be retained in the oxygen ion conducting ceramic. Moisture and other impurities, such as carbon dioxide, will be largely discharged from the system with the non-absorbed waste gas stream. Some $H_2O$ and $CO_2$ may be decomposed by the oxygen ion conducting ceramic with retention of oxygen therein.

During the oxygen reaction stage of the process, the oxygen ion conducting ceramic in vessel A is maintained at a temperature in the range of about 300 to 1400° C. Initial heating of the oxygen ion conducting ceramic is accomplished by heating the feed air as it passes through heat exchanger 42, before it enters vessel A. As an alternative, for example, at initial start-up of the system, heating of the feed air or oxygen ion conducting ceramic can be accomplished by any suitable means, such as by external heating devices. When it is desired to heat the oxygen ion conducting ceramic, in addition to or instead of heating the incoming air, any suitable method may be used. Such methods include, for example, electric heating means, incorporating the reaction zone in a furnace zone, or combusting fuel and passing the hot combustion gases through the reaction zone prior to introduction of air thereto. The method used to heat the oxygen ion conducting ceramic in the reaction vessels at initial start-up of the system is a matter of choice and forms no part of this invention.

Once the oxygen ion conducting ceramic in vessel A reaches the desired reaction temperature, it is generally not necessary to continue applying heat to the reaction zone to maintain the oxygen ion conducting ceramic at the desired oxygen reaction and partial oxidation reaction temperature. The heat of oxygen reaction during the oxygen step and the heat of reaction during the partial oxidation step are adequate to maintain the desired temperature. Distribution of heat in the reaction zone can be facilitated, if desired, by incorporating a material having a high thermal conductivity and/or high heat capacity into the reaction zone. This can be accomplished by mixing or sandwiching, i.e. layering, the oxygen ion conducting ceramic with a high temperature stable material, such as a heat conducting ceramic material or a particulate metal material. Heat flow in the reaction zone can also be accomplished by inserting strips or rods of metallic material in the vessel, upstream or downstream of the reaction zones. If it is desirable or necessary to remove heat from the reaction zone to prevent excessive heating of the oxygen ion conducting ceramic contained therein, this can be accomplished by means of the above-described heat transmission means.

In any event, the air feed stream entering vessel A passes downward through the oxygen ion conducting ceramic contained therein, and as it does so, oxygen reacts with the oxygen ion conducting ceramic. Non-reacted gases, comprised substantially of nitrogen and argon when air is the feed, leave vessel A through line 62 and pass sequentially through heat exchanger 44, valve 24, line 68, valve 40 and ultimately through waste gas line 10. The non-reacted gases may be collected as a byproduct gas stream, or can be discharged to the atmosphere. As the oxygen step proceeds in vessel A, the oxygen retained in the oxygen ion conducting ceramic forms a front which advances through the bed of oxygen ion conducting ceramic toward the non-reacted product outlet end of vessel A.

While the oxygen step is taking place in vessel A, the partial oxidation step is initiated and carried out in vessel B. The hydrocarbon gas contacts the hot oxygen-enriched ceramic in vessel to produce the desired partial oxidation gas product, which is generally a mixture of hydrogen and carbon monoxide. The product gas stream may also contain other gaseous by-products, such as, carbon dioxide and moisture, but the concentration of these by-products can be minimized by maintaining optimum reaction conditions in the reaction vessel. When the hydrocarbon is fed along with steam, substantial amounts of $CO_2$ may be formed due to a water gas shift reaction ($CO + H_2O \rightleftharpoons CO_2 + H_2$). The hot reaction product gases pass out of vessel B through line 34, pass through heat exchanger 42, then through valves 38 and 40 and ultimately pass through line 8 to storage or downstream processing units. As the partial oxidation reaction progresses in vessel B, the oxygen ion conducting ceramic in this vessel is depleted of oxygen and thereby regenerated.

At a predetermined point in the first stage of the process, such as, when the oxygen-enriched ceramic reaches a desired point in vessel A, or when all of the oxygen enriched ceramic in vessel B is regenerated, the first stage of the cycle is terminated and the second stage begins. By proper sizing of the reaction vessels and careful control of the reactant gas flow rates, the process can be designed so that the oxygen step in vessel A reaches its desired end point at substantially the same time as when all of the oxygen enriched ceramic in vessel B is regenerated. Alternatively, if the oxygen step in vessel A reaches its desired end point before the oxygen-enriched ceramic in vessel B is completely regenerated, or vice versa, the completed part of the first stage of the process can be terminated and further activity in that vessel can be suspended until the other part of the first stage reaches its desired end point.

Upon completion of the first stage of the process, the second stage is initiated. During the second stage, valves 22, 30, 38, 16, 32 and 24, and optionally valve 12, are open and all other valves are closed. Valve 40 is switched into position whereby valve 38 output is now in fluid connection with waste line 10 and valve 24 output is in fluid connection with product line 8. Air is introduced into the system through line 2, and passes through valve 22, through lines 52 and 74, through valve 30 and heat exchanger 44 and enters vessel B through line 64. As the air passes through vessel B, oxygen reacts with the regenerated perovskite ceramic in this vessel. Non-reacted gas passes out of vessel B through line 34, through heat exchanger 42, through valve 38, through valve 40, and ultimately leaves the system through waste gas line 10.

Meanwhile, the partial oxidation process is initiated and carried out in vessel A. During this stage of the cycle, hydrocarbon gas is introduced into vessel A through line 4, valve 16, line 48, line 66, valve 32, heat exchanger 42 and finally through line 58, in that order, while simultaneously introducing steam through line 6, valve 12 and line 50 into line 66 carrying the hydrocarbon feed. The hydrocarbon gas continues to flow to vessel A where it contacts the hot oxygen-enriched ceramic to produce the desired partial oxidation gas product. The hot reaction product gases pass out of vessel A through line 62, heat exchanger 44, valve 24, line 68, valve 40, and finally through product line 8.

When the desired end point is reached, the second stage of the process (and the current cycle) ends and the next cycle begins with vessel A in oxygen reaction mode and vessel B in partial oxidation reaction mode.

It may be desirable to purge the vessels after completing the partial oxidation step of the process. The purge of vessels A and B can be accomplished by respectively opening valves 12 or 14 and valves 30 or 32 and by introducing steam or another compatible gas to the vessels via lines 50 and 66 or via lines 56, 70 and 74.

Alternatively, the consecutive steps of oxygen reaction, production and purge can be arranged among vessels A and B, such that at any given time at least one of vessels A or B is producing the desired product gas. This can be accomplished by proper selection of flow rates of different streams and step times.

It will be appreciated that it is within the scope of the present invention to utilize conventional equipment to monitor and automatically regulate the flow of gases within the system so that it can be fully automated to run continuously in an efficient manner.

The invention is further illustrated by the following example in which, unless otherwise indicated, parts, percentages and ratios are on a volume basis.

EXAMPLE 1

This experiment was carried out in a fixed-bed reactor similar to the system illustrated in FIG. 1, except that a single reactor was used. The reactor, which has an inner diameter of 1.6 inches and a length of 24 inches, was packed with about 200 cc of alumina (50 wt. %) supported $La_{0.0}Sr_{0.2}Ni_{0.4}Co_{0.4}Fe_{0.2}O_3$ perovskite-type ceramic material. The ceramic material was in the form of extrudates, about 1/8" in diameter and 1/4" in length. A PLC and a computer controlled the operation of the reactor system, and feed flow rates and the reactor temperature were controlled by mass flow controllers and temperature controllers.

The cycle of the process tested in the experiment contained five steps: (1) oxygen reaction step using low pressure air; (2) pressurization of the reactor with steam; (3) partial oxidation using high pressure methane and steam; (4) high pressure steam purge of the reactor; and (5) depressurization of the reactor. In the first step, air at about 1.4 bara (5 psig) and at a flow rate of 9.6 slpm was fed into the reactor for 30 seconds. In the second step, steam was introduced into the reactor at a flow rate of 9.3 slpm for 20 seconds to build up the pressure in the reactor to about 4.5 bara (50 psig). There was no effluent during this step. During the third step, a flow containing a mixture of $CH_4$ (at 4 slpm) and steam (at 6.2 slpm) at a pressure of about 6.5 bara (80 psig) was introduced into the reactor for 30 seconds. Pure steam, at about 6.5 bara (80 psig), was fed into the reactor during the fourth step for 15 seconds. The pressure in the reactor was released to about 1.4 bara (5 psig) during the fifth step, which took about 10 seconds. The above steps were repeated in the next cycle. The reactor temperature varied from about 750 to 900° C. with the highest temperature occurring at the end of the first step and the lowest temperature occurring at the end of the fifth step. Nitrogen was the primary compound in the effluent of the first step while the effluent of the third and fourth steps contained hydrogen, carbon monoxide and carbon dioxide with an average composition of 70.9% $H_2$, 14.5% CO and 14.7% $CO_2$ (on a dry basis). The average product flow was 14 slpm. The effluent in the fifth step was primarily steam. Methane conversion was higher than 98%.

EXAMPLE 2

The experiment was carried out over the same ceramic material and in the same fixed-bed reactor described in the example 1. The cycle of the process tested in this experiment contained two steps: (1) oxygen reaction step using air at 6.5 bara (80 psig); (2) partial oxidation step using methane and steam at 6.5 bara (80 psig). In the first step, air at a flow rate of 13.8 slpm was fed into the reactor for 30 seconds. During the second step, a flow containing a mixture of $CH_4$ (at 7.95 slpm) and steam (at 16.8 slpm) was introduced into the reactor for 30 seconds. The above steps were repeated in the next cycle. The reactor temperature varied from about 815 to 925° C. with the highest temperature occurring at the end of the first step and the lowest temperature occurring at the end of the second step. Nitrogen was the primary compound in the effluent of the first step while the effluent of the second step contained hydrogen, carbon monoxide, carbon dioxide and methane with an average composition of 69.0% $H_2$, 19.1% CO, 8.65% $CO_2$ and 3.22% $CH_4$ (on a dry basis). The average product flow was 20.5 slpm. Methane conversion was 89.6%. The above examples illustrate that low pressure or high pressure air can be effectively used in the oxygen reaction step. Additionally, it demonstrates that methane can be reacted with the oxygen enriched perovskite at an elevated temperature to produce hydrogen and carbon monoxide as principal reaction products.

The examples illustrate that low pressure or high pressure air can be effectively used in the oxygen reaction step. Additionally, it demonstrates that methane can be reacted with the oxygen enriched perovskite at an elevated temperature to produce hydrogen and carbon monoxide as principal reaction products.

Although the invention has been described with particular reference to specific equipment arrangements and to specific experiments, these features are merely exemplary of the invention and variations are contemplated. For example, the process can be carried out in one vessel, two vessels, or multiple vessel systems comprising three or more vessels operated, for example, in or out of phase, countercurrently, or co-currently. As another alternative to the above-described process, the invention can be practiced by conducting the hydrocarbon partial oxidation step in the liquid phase. Furthermore, when oxygen-containing gas and hydrocarbon feed are introduced at different pressures, the process will include pressurization and de-pressurization steps as discussed in Example 1. The scope of the invention is limited only by the breadth of the appended claims.

What is claimed is:

1. A process for the partial oxidation of at least one hydrocarbon comprising the steps of:
   (a) contacting an oxygen ion conducting ceramic in particulate form in a reactor with an oxygen-containing gas at a temperature in the range between about 300 and 1400° C. and at a pressure in the range between about 1 and 50 bara, wherein oxygen from said oxygen-containing gas is reacted with said ceramic, thereby producing an oxygen-enriched ceramic; and
   (b) contacting said oxygen-enriched ceramic in said reactor with a hydrocarbon at a temperature in the range between about 300 and 1400° C., thereby producing a product gas through the reaction between said oxygen-enriched ceramic and said hydrocarbon.

2. The process of claim 1, wherein step (b) is conducted at a pressure of between about 1 and 50 bara.

3. The process of claim 2, wherein step (b) is conducted at a pressure between about 3 and 35 bara.

4. The process of claim 1, wherein said product gas is a gas comprising hydrogen and carbon monoxide.

5. The process of claim 1, wherein said oxygen ion conducting ceramic is selected from the group consisting of: (1) perovskite substances having the structural formula $ABO_3$, where A is at least one metal ion capable of occupying the 12-coordinate sites of the perovskite and B is at least one metal ion capable of occupying the 6-coordinate sites of the perovskite; (2) ceramic substances selected from the group consisting of $Bi_2O_3$, $ZrO_2$, $CeO_2$, $ThO_2$, $HfO_2$ and mixtures thereof, the ceramic substance being doped with CaO, rare earth metal oxides or mixtures thereof; (3) brownmillerite oxide; and (4) mixtures thereof.

6. The process of claim 5, wherein said oxygen ion conducting ceramic is a perovskite substance having the structural formula $ABO_3$.

7. The process of claim 6, where A is at least one metal ion selected from alkali, alkaline earth and rare earth ions, and B is at least one metal atom selected from transition metal ions.

8. The process of claim 7, where A is La, Sr, Ca, Ba, Mg, or mixtures thereof, and B is Co, Mn, Cr, Ni, Fe, or mixtures thereof.

9. The process of claim 1, wherein said oxygen-containing gas is air.

10. The process of claim 1, wherein step (a) is carried out at a temperature between about 600 and 1000° C. and a pressure between about 1 and 2 bara.

11. The process of claim 1, wherein step (b) is carried out at a temperature between about 600 and 1000° C.

12. The process of claim 1, further comprising the step of purging said product gas from said reactor following step (b) with a gas selected from the group consisting of: steam, carbon dioxide, nitrogen, argon, helium, and mixtures thereof.

13. The process of claim 1, wherein said at least one hydrocarbon is selected from the group consisting of: aliphatic hydrocarbons, cycloaliphatic hydrocarbons, aromatic hydrocarbons, and mixtures thereof, provided that said hydrocarbon has a carbon number in the range between about 1 and 12.

14. The process of claim 13, wherein said at least one hydrocarbon is selected from the group consisting of: methane, methanol, natural gas, naphtha, gasoline, diesel, and mixtures thereof.

15. The process of claim 1, further comprising at least one particulate material other than said ceramic in said reactor.

16. The process of claim 15, wherein said particulate material has a heat capacity greater than that of said ceramic.

17. The process of claim 16, wherein said particulate material is placed upstream, downstream or both upstream and downstream of said ceramic.

18. The process of claim 16, wherein said particulate material is mixed with said ceramic.

19. The process of claim 18, wherein said ceramic is supported on said particulate material.

20. The process of claim 1, further comprising a step of contacting said ceramic with a moderating agent during step (b).

21. The process of claim 20, wherein said moderating agent is selected from the group consisting of steam, carbon dioxide and mixtures thereof.

22. The process of claim 1, further comprising repeatedly performing steps (a) and (b) in sequence, or (b) and (a) in sequence.

23. A continuous process for the partial oxidation of at least one hydrocarbon comprising the steps of:
  (a) in a first reactor, contacting a first oxygen ion conducting ceramic with an oxygen-containing gas at a temperature in the range between about 300 and 1400° C. and at a pressure in the range between about 1 and 50 bara, wherein oxygen from said oxygen-containing gas reacts with said first ceramic, thereby producing a first oxygen-enriched ceramic; and contacting said first oxygen-enriched ceramic with said hydrocarbon at a temperature in the range between about 300 and 1400° C., thereby producing a first product gas; and
  (b) in a second reactor, contacting a second oxygen ion conducting ceramic with an oxygen-containing gas at a temperature in the range between about 300 and 1400° C. and at a pressure in the range between about 1 and 50 bara, wherein oxygen from said oxygen-containing gas reacts with said second ceramic, thereby producing a second oxygen-enriched ceramic; and contacting said second oxygen-enriched ceramic with said hydrocarbon at a temperature in the range between about 300 and 1400° C., thereby producing a second product gas.

24. The process according to claim 23, wherein said first reactor is 180° out of phase with said second reactor, whereby either:
  (a) said first product gas is being formed in and removed from said first reactor while oxygen from an oxygen-containing gas is reacting with said second ceramic in said second reactor; or
  (b) oxygen from an oxygen-containing gas is reacting with said first ceramic in said first reactor while said second product gas is being formed in and removed from said second reactor.

25. The process according to claim 23 wherein three or more reactors are used in said process.

* * * * *